United States Patent [19]

Esposito et al.

[11] Patent Number: 5,348,741
[45] Date of Patent: * Sep. 20, 1994

[54] VECTOR FOR RECOMBINANT POXVIRUS EXPRESSING RABIES VIRUS GLYCOPROTEIN

[75] Inventors: Joseph J. Esposito, Atlanta, Ga.; Bernard Moss, Bethesda, Md.; Kathleen Brechling, Raleigh, N.C.

[73] Assignee: The United States of America as represented by the Department of Health and Human Services, Washington, D.C.

[*] Notice: The portion of the term of this patent subsequent to Nov. 30, 2010 has been disclaimed.

[21] Appl. No.: 944,743

[22] Filed: Sep. 14, 1992

Related U.S. Application Data

[63] Continuation of Ser. No. 445,131, Nov. 30, 1989, abandoned, which is a continuation of Ser. No. 10,424, Feb. 3, 1987, abandoned.

[51] Int. Cl.$^5$ ............................................. A61K 31/12
[52] U.S. Cl. .................................... 424/199.1; 435/5; 435/172.3; 435/235.1; 435/320.1; 935/32; 935/65; 424/224.1; 424/232.1
[58] Field of Search ............ 435/5, 172.3, 235.1, 435/320.1; 424/89; 935/32, 65, 81

[56] References Cited

U.S. PATENT DOCUMENTS

| | | | |
|---|---|---|---|
| 4,603,112 | 7/1986 | Paoletti et al. | 435/172.3 |
| 4,631,191 | 12/1986 | Dale et al. | 424/89 |
| 4,652,629 | 3/1987 | Patrick et al. | 530/403 |
| 4,719,177 | 1/1988 | Baltimore et al. | 435/172.3 |
| 5,017,487 | 5/1991 | Stunnenberg et al. | 435/172.3 |

FOREIGN PATENT DOCUMENTS 0182442  5/1986  European Pat. Off. ................. 435/5

OTHER PUBLICATIONS

Davis, et al., *Microbiology*, 2nd ed., Harper & Row, Hagerstown, Md., pp. 1258–1261 (1973).
Esposito, et al., Virus Genes 1:1, 7–21, 1987.
Mackett, et al., *DNA Cloning* 2: 191–211, 1985.
Smith, et al., Laboratory Techniques in Rabies Appendix 5 pp. 354–357 1973.
Thomas, et al., *Archives of Virology* 49:217–227, 1975.
Parsons, et al., *Virology* 161:45–53, 1987.
Rosel, et al., *Journal of Virology*, 60:436–449, 1986.
Weir, et al., *Journal of Virology* 61:75–80, 1987.
Cochran, et al., *Journal of Virology*, 54:30–37, 1985.
Coupar et al, Eur. J. Immunol., vol. 16, pp. 1479–1487 (1986).
Baer, et al, *American Journal of Epidemiology* 93:487–490 1971.
*World Health Organization Technical Report Series* 709:57–62, 1984.
Lodmell et al, Journal of Virology, vol. 65, No. 6, pp. 3400–3405 (1991).
Sumner et al, Virology, vol. 183, pp. 703–710 (1991).
Lafon et al, J. Gen. Virol., vol. 68, pp. 3113–3123 (1987).
Dietzshold et al, Proc. Natl. Acad. Sci. USA, vol. 84 (24), pp. 9165–9169 (1987).
Pearson et al, Virology, vol. 180 (2), pp. 561–566 (1991).
Yaye F. Hermans, *Bacteriological Proceedings* V12, pg. 117, 1964.

(List continued on next page.)

Primary Examiner—Esther L. Kepplinger
Assistant Examiner—Donna C. Wortman
Attorney, Agent, or Firm—Knobbe, Martens, Olson & Bear

[57] ABSTRACT

A plasmid vector has been constructed for producing unique vaccinia virus recombinant expressing the gene for rabiesvirus glycoprotein in cells. The recombinant induces production of glycoprotein in substantial amounts for immunization against rabies. Such recombinant could be applied for the production of anti-rabies vaccine and of G antigen antibody and related immunological reagents for research or diagnostic purposes.

20 Claims, 5 Drawing Sheets

OTHER PUBLICATIONS

Alexander, et al., *Journal of Wildlife Diseases* 8:119–126, 1972.
Esposito, et al., *Virology* 143:230–251, 1985.
E. Krag Andersen *Proc. Symposium or Smallpox*, 53–64, 1969.
Gezondheidstraad, et al. *Symp. Series Immunbiol.* 19:235–242, 1972.
Kieny, et al., (1984) *Nature* 312:163–166 "Expression of Rabies Virus Glycoprotein from a Recombinant Vaccinia Virus".
Wiktor, et al, (1984) *Proc. Natl. Acad. Sci. USA* 81:7194–7198 "Protection from rabies by a Vaccinia Virus Recombinant Containing the Rabies Virus Glycoprotein Gene".
Yelverton, et al, (1983) *Science* 219:614–620 "Virus Glycoprotein Analogs: Biosynthesis in *Escherichia coli*".
Abstract #86-01678 of EPO 117657.

FIGURE 2

```
VECTOR              SmaI
                BamHI    EcoRI
pGS62     P7.5....CG GAT CCC CGG GAA TTC.....
                                        met val pro gln
pGS62-JE-E        CG GAT CCC CGG GAA TTC ATG GTT CCT CAG
                                        met val pro gln
pGS62-JE-I    CGG ATC CCC GGG AAT TCG GGC ATG GTT CCT CAG

**       EcoRI
pKB3      P11................TA TAA ATG AAT TCA.....
                              **       met asn ser gly val pro gln
pKB3-JE-8                     TA TAA ATG AAT TCG GGG GTT CCT CAG
                              **       met asn ser gly met val pro gln
pKB3-JE-13                    TA TAA ATG AAT TCG GGC ATG GTT CCT CAG
                     *  *  ++ +        met val pro gln
pKB26              T ATA AAA GAA TTC ATG GTT CCT CAG
                              **       met val pro gln
pKB36                         TA TAA ATG GTT CCT CAG met val pro gln....CVS Rabiesvirus
pRABpreG..........GAA TTC ATG GTT CCT CAG         glycoprotein
                  EcoRI
```

VECTOR FOR RECOMBINANT POXVIRUS EXPRESSING RABIES VIRUS GLYCOPROTEIN

This application is a continuation, of application Ser. No. 07/445,131 filed on Nov. 30, 1989, now abandoned, which is a continuation of Ser. No. 07/010,424, filed on Feb. 3, 1987, now abandoned.

BACKGROUND OF THE INVENTION

1. Technical Field

The present invention is related to a viral vaccine against rabies and use of the virus for producing rabiesvirus immunobiologicals. More particularly, the present invention is related to a genetically engineered plasmid vector that has been used to construct a unique vaccinia poxvirus infectious recombinant for expressing in animals or in tissue cultures part or all of the gene for rabiesvirus glycoprotein. Such a recombinant employing vaccinia or other poxviruses, could be used for production of rabies vaccine, live or inactivated, as well as for production of rabiesvirus glycoprotein antigen, antibody or other related biochemical or immunological reagents.

2. State of the Art

Rabies vaccines presently in use generally contain preparations of inactivated or attenuated live rabiesvirus. Such preparations might be relatively costly, biologically unstable or produce vaccinal side effects. Recently, the cloned cDNA of the glycoprotein (G) gene of the ERA strain of rabiesvirus (Anilionis et al. 1981 Nature 294:275-278) was expressed by infecting mammalian cell cultures with a recombinant of the Copenhagen strain of vaccinia virus (Kieny et al. 1984 Nature 312:163-166; Wiktor et al. 1984 PNAS 81:7194-7198). To produce the recombinant, the G cDNA had been directed into the vaccinia thymidine kinase (TK) locus essentially by genetic recombination method (Mackett et al. 1982 PNAS 79:7415-7419; Mackett et al. 1984 J. Virol. 49:857-864) with a bacterial plasmid construct that contained cDNA of ERA G flanked by vaccinia TK sequences. Expression of G was regulated by having inserted proximal to G cDNA the commonly used vaccinia gene promoter for the 7.5 kilodalton (kD) protein (Mackett et al. 1984 ibid.). Mice and rabbits that were vaccinated with this recombinant virus (VVTGgRAB26D3) produced neutralizing antibodies and were protected against rabiesvirus challenge. However, the Copenhagen strain of vaccinia, the vector for expression of the rabiesvirus strain ERA G cDNA, is most likely to be unsuitable for vaccine purposes because it has been associated with a relatively high frequency of encephalitic vaccinal complications in humans when used for immunoprophylaxis of smallpox (Polak 1973 Int. Symp. on Smallpox Vaccine, 1972 Bilthoven, 19:235-242, Karger, Basil; vonMagnus 1973 Int. Symp. on Smallpox Vaccine, 1972 Bilthoven 19:227-233, Karger, Basil) and has relatively more apparent pathogenicity for laboratory animals compared to other vaccinia strains (Andersen 1969 Proc. Symp. on Smallpox, pp. 53-64, Yugoslav Acad. Sci., 1969 Zagreb, Yugoslavia). Hence, the need remains to provide for humans and animals an efficacious vaccine against rabies that would be potent, less perishable, less costly and having diminished or no vaccinal side effects compared to the presently utilized rabies vaccines. A vaccinia—based vaccine, such as strains Lister and New York Board of Health which have been used with relatively low side effects during the eradication of smallpox, appears to possess such attributes. (Arita and Fenner, 1985, "Vaccinia Virus as Vectors for Vaccine Antigens," pp. 49-60, G. Quinnan ed., Elsevier, N.Y. Recombinants derived with these strains and used for vaccine could also be readily adapted for production of related antigen, antibody and other immunobiological reagents. However, whether recombinants made with the more attenuated vaccine strains could protectively immunize against rabiesvirus infection, cannot be a priori predicted. Increased expression of immunogen genes such as rabiesvirus G could be gained by incorporating poxvirus DNA control elements that would regulate higher levels of protein production than currently achieved by use of promotor $P_{7.5}$.

SUMMARY OF INVENTION

It is, therefore, an object of the present invention to provide a plasmid vector for producing a unique infectious recombinant virus that contains a relatively strong but late vaccinia promoter for increased expression of coding sequences for rabiesvirus glycoprotein.

It is another object of the present invention to apply such vector to provide a unique vaccinia virus recombinant expressing gene for rabiesvirus glycoprotein in order to produce efficacious vaccine against rabies with improved properties in selected applications.

It is a further object of the present invention to utilize the plasmid vector of the present invention to produce recombinant viruses for production of rabiesvirus glycoprotein antigens, antibodies and related biochemical and immunobiological reagents.

Other objects and advantages of the present invention will become evident as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 2 shows the different DNA primary structure and deduced amino acid sequences at the junction of the promoter and the rabiesvirus glycoprotein coding sequences for the six vectors. (Plasmids derived as described in FIG. 1 were examined by primer extension dideoxynucleotide supercoil sequence determination to appropriately select vectors for transfecting vaccinia infected cells). The putative transcript start site (*) determined for the 11 kD gene and the mutagenized site (+) in pKB14 for deriving pKB26 are indicated;

FIGS. 3-1, 3-2, 3-3, 3-4, 3-5, 3-6, 3-7 and 3-8 indicate the qualitatively different amounts of rabiesvirus G antigen produced in cells infected with recombinant viruses ("v" prefix) produced with vector plasmids ("p" prefix) described in FIGS. 1 and 2. Antigen was detected by direct immunofluorescence microscopy examination of mouse ascites anti-G IgG monoclonal antibody reactivity with acetone-fixed monolayers of CV-1 cells at 18 h postinfection (input multiplicity of 1 PFU per cell), respectively with virus recombinants (panels 1-7) vGS62-JE-E, vGS62-JE-I, vKB3-JE-8, vKB3-JE-13, vKB26, vKB36 and mock infected. Panel 8 shows cell surface direct immunofluorescence appearance representative of CV-1 cells infected with a recombinant virus (vKB3-JE-13 shown) and then reacted with anti-G mAB-IgG followed by fixation at 18 h postinfection with paraformaldehyde; and FIG. 4 shows Western blot antigenic analysis of rabiesvirus glycoprotein. Proteins of washed, denatured infected cells monolayers were separated by 12% discontinuous SDS-polyacrylamide gel electrophoresis and then electroblotted onto nitrocellulose filter paper. Blots were treated with rabbit anti-G serum and then with $^{125}$I protein-A prior to autoradiography. Lanes 1-8 show 143 B cells ($10^6$ cells, input multiplicity (MOI) 25 PFU per cell) 18 h postinfection, respectively with NYBH vaccinia virus, vGS62-JE-E, vGS62-JE-I, vKB3-JE-8, vKB3-JE-13, vKB26, vKB36 and mock infected. Lanes 9 and 10 show respectively, CVS rabies virus and mock infected NA cells ($10^6$ cells, MOI=2 PFU per cell, 44 h postinfection). Lane 11 shows $10^5$ cells infected as in lane 9. Lane 12 shows an extended exposure of lane 9 for better visualization of the CVS glycoprotein (64-62 kD).

DETAILED DESCRIPTION OF INVENTION

Figure 1A:
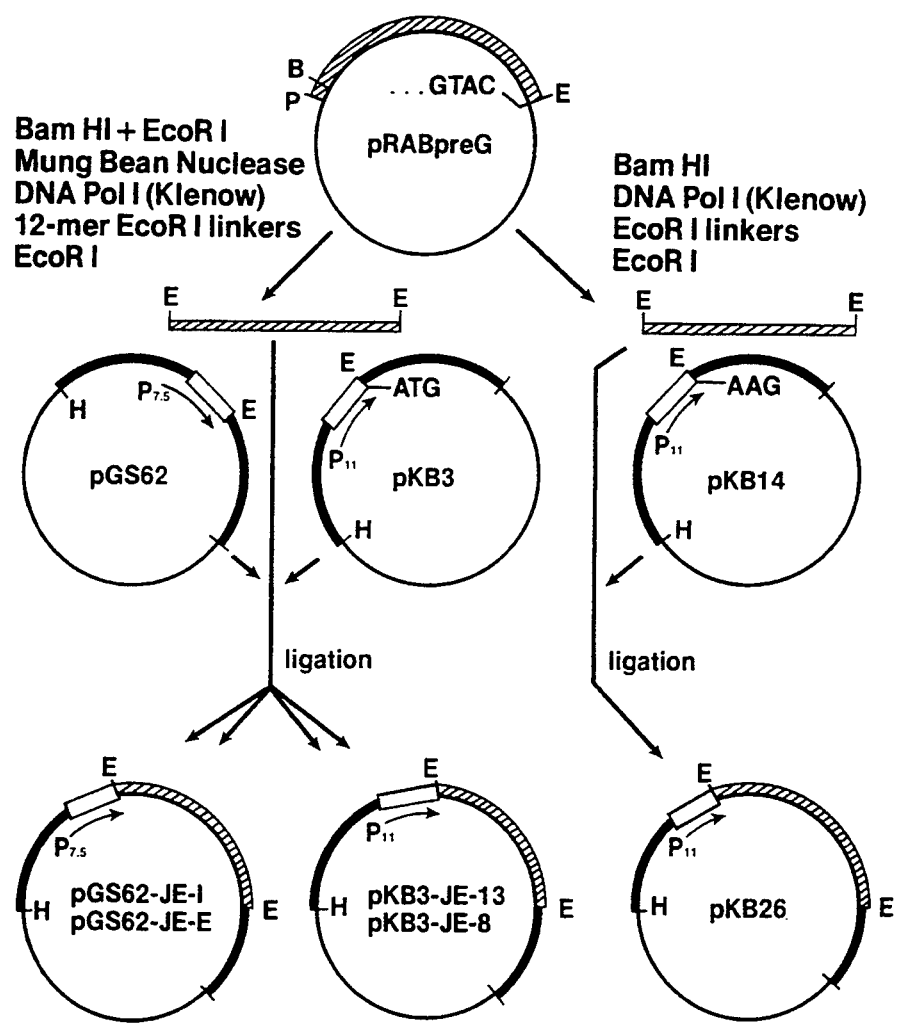
FIGS. 1A and 1B show schematic construction of the invention pKB3-JE-13 and five other bacterial plasmid vectors derived for comparative analyses. (A) The complete CVS rabiesvirus glycoprotein 1600 bp (EcoRI to BamHI) coding sequence cDNA (rab-G) was modified by linker addition at both ends to arrange the start codon ATG of rab-G in reading frame with the 11 kD protein start codon ATG in pKB3, a derivative of commonly used pUC13 with TK sequences (thickened line) flanking the 200 bp vaccinia late promoter, $P_{11}$. Fragment rab-G also was inserted at the single EcoRI site in pGS62, a derivative of pGS20 that contained TK sequences flanking vaccinia promoter, $P_{7.5}$. An EcoRI linker was added only at the BamHI end for insertion into pKB14, a pKB3 derivative mutagenized by an adenosine substitution at thymidine in the 11 kD protein start codon described above. After transformation of E. coli HB101 cells, ampicillin-resistant colonies were screened by hybridization with rab-G sequences and insert orientation was determined by electrophoresis of PstI and XbaI digestion of plasmid preparations. (B) The latter modified rab-G fragment also was inserted into the single EcoRI site in the bacteriophage replicative form mpKB19, a derivate of commonly used M13mp9 that contained $P_{11}$. Oligonucleotide mediated mutagenesis of the junction of $P_{11}$ and rab-G was performed in order to delete the intervening residue 5'-ATGAATTC-3' and to shift the rab-G translation start codon into reading frame forming mpKB25. A 1750 bp XbaI-EcoRI fragment from mpKB25 containing 100 bp of $P_{11}$ fused to rab-G was inserted appropriately into pKB3 (XbaI-EcoRI cleaved) to produce vector pKB36. After primer extension nucleotide sequence determination (FIG. 2) to establish appropriate promoter-rab-G nucleotide junctions, vectors pGS62-JE-E, pGS62-JE-I, pKB3-JE-8, pKB3-JE-13 (the invention claimed herein), pKB26 and pKB36 were used separately to transfect vaccinia-infected cells.

The above and various other objects and advantages of the present invention are achieved by a novel recombinant designated vKB3-JE-13 (derived with plasmid vector pKB3-JE-13) described more fully hereunder.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

A late pox virus (e.g. vaccinia) promoter is defined herein as a DNA segment that includes nucleotide sequences which regulate gene expression and are functionally active after but not before the replication of virus DNA in infected cells. Examples of late genes are described by Rosel et al. 1986 J. Virol 60:436-449. Too few late genes have been analyzed in detail to develop a promoter consensus nucleotide sequence, generally such promoters reside immediately upstream of coding sequences.

The term "orthopoxvirus" as used herein is defined to include any poxvirus, other than vaccinia virus, which can be employed to produce the recombinant virus in accordance with the methodology described herein.

The general approach for constructing the recombinant virus in accordance with the present invention comprises selecting a strain of vaccinia virus historically having shown considerably diminished vaccinal side effects, such as the New York Board of Health (NYBH) strain of vaccinia virus, then directing the insertion of glycoprotein G gene coding sequence of rabiesvirus Challenge Virus Standard (CVS) into the TK locus of this virus by standard DNA recombination methodology well known in the art.

Although other strains of vaccinia could be utilized, the United States licensed NYBH strain was chosen as a vector because it was demonstrated during the eradication of smallpox that this strain (as well as the Lister strain) when used as smallpox vaccine showed considerably diminished vaccinal side effects relative to all other strains (Arita & Fenner, 1985, "Vaccinia Virus as Vectors for Vaccine Antigens", pp. 49-60, Quinnan, ed, Elsevier, N.Y.). The G cDNA of CVS rabiesvirus was chosen because this strain is sometimes used as a seed for inactivated rabies vaccine and the live virus is generally regarded to be like naturally occurring street strains of rabiesvirus. The cDNA for CVS rabiesvirus G (Yelverton et al 983 Science 219:614-620) was obtained as a bacterial plasmid preparation (pRab pre G Pst lig3) from Genentech, Inc., South San Francisco, Calif. (see below). It is noted that the CVS G cDNA is different from ERA G cDNA in nucleotide sequence. Recombinatorial insertion of CVS G cDNA at the vaccinia TK locus was accomplished by transfection of vaccinia infected cell cultures with a novel plasmid construct pKB3-JE-13, a derivative of commonly used E. coli plasmid pUC-13 in which was incorporated a cassette comprised of vaccinia TK nucleotide sequences flanking promoter $P_{11}$ fused to G coding sequences. The promoter from the vaccinia gene for the 11 kD protein was used in pKB3-JE-13 in order to regulate expression of the downstream adjacent G coding sequences. A unique feature of the present invention is the insertion of this particular $P_{11}$ promoter that apparently regulates higher levels of expression of inserted DNAs than the promoter $P_{7.5}$ for the 7.5 kD protein, an aspect which could not have been predicted a priori.

During construction of the present invention, plasmid designated pKB3-JE-13, the fusion of promoter and G sequences was facilitated by addition of commonly used EcoRI linker sequences onto the ends of the G sequences. Analysis of the plasmid prior to its use in transfection showed (vide infra) that the junction of the 11 kD gene promoter and the CVS G cDNA contained the linker sequences. The presence of linker nucleotides added 4 amino acids at the aminoterminal signal peptide region of G compared to standard CVS virus G coding sequences, serving inter alia to earmark vectors containing this construct. It is noted that the presence of these extra nucleotides showed no apparent effect on the cDNA expression. In order to construct pKB3-JE-13, routine recombinant DNA manipulations were performed following standard techniques (Chen & Seeburg 1985 DNA 4:165-170; Maniatis et al. 1982 Molecular cloning: A laboratory manual, Cold Spring Harbor Laboratory, New York; Messing 1983 Methods Enzymol. 101:20-78; Silhavy et al. 1984 Experiments with gene fusions, Cold Spring Harbor Laboratory, New York). The novel plasmid pKB3-JE-13 thus obtained has been deposited into the American Type Culture Collection, Rockville, Md., under accession number 40280. Upon request the Commissioner of Patents shall have access to the deposit which, of course, shall be viably maintained for a period of 30 years or 5 years after the last request or for the effective life of the patent whichever is longer and upon issuance of a patent shall be made available to the public without restriction, of course, in accordance with the provisions of the law.

Preferred methods and materials are now described.

MATERIALS AND METHODS

Viruses and cells

The thymidine kinase positive (TK) NYBH strain of vaccinia virus and TK recombinants were propagated in monkey kidney CV-1 cells or human 143 B TK cells (Rhim et al., 1975, Int. J. Cancer 15:23-29) maintained in high glucose Dulbecco modified Eagle medium (DME) or in HeLa cells maintained in Eagle spinner medium. For TK plaque assays on 143 B cells, DME overlays contained 1% low melting point agarose (Marine Colloids, Inc.) and 30 micrograms 5-bromodeoxyuridine (BUdR) per ml. Vaccinia virions (thrice plaque purified) for antigen assays and immunizations were purified from the cytoplasm of infected cells by centrifugation (Beckman SW28 rotor, 15 k rpm, 80 min) through 12 ml of 40% (w/w) sucrose onto a 0.1 ml glycerol pad. Pelleted virions were homogenized (Potter-Elvjhem homogenizer, Tekmar, Inc.) and further purified by velocity sedimentation in sucrose gradients (20 to 40% w/w; 12 k rpm, 40 min) (Esposito et al., 1978, Virology 89:53-66). Rabiesvirus infected mouse neuroblastoma (NA) cells (gamma irradiated, $4 \times 10^7$ cells per ml) were obtained from Rabies Investigations Laboratory, Centers for Disease Control (CDC), Atlanta, Ga.

Construction of plasmid vectors

The pBR322 derivative pRAB91 (Yelverton et al., 1983 Science 219:614-620) contained a dG/dC-tailed (PstI site bounded) insert cDNA prepared by reverse transcription of CVS G mRNA. The insert had been modified at the 5'-end of the sense strand by using a synthetic oligonucleotide (Yelverton et al., ibid.) to replace the PstI site with an EcoRI site and provide an ATG translation initiation codon absent from the otherwise complete G coding sequence. The repaired plasmid pRabpreGpst lig3 (designated pRABpreG in FIG. 1A) containing a 2040 base pair (bp) DNA encoding G inserted in the ampicillin locus (EcoRI to PstI) of pBR322 was obtained from Genentech, Inc., South San Francisco, Calif. Cleavage of pRABpreG with EcoRI and BamHI released a 1650 bp fragment that contained the complete G coding sequence.

Figure 1B:
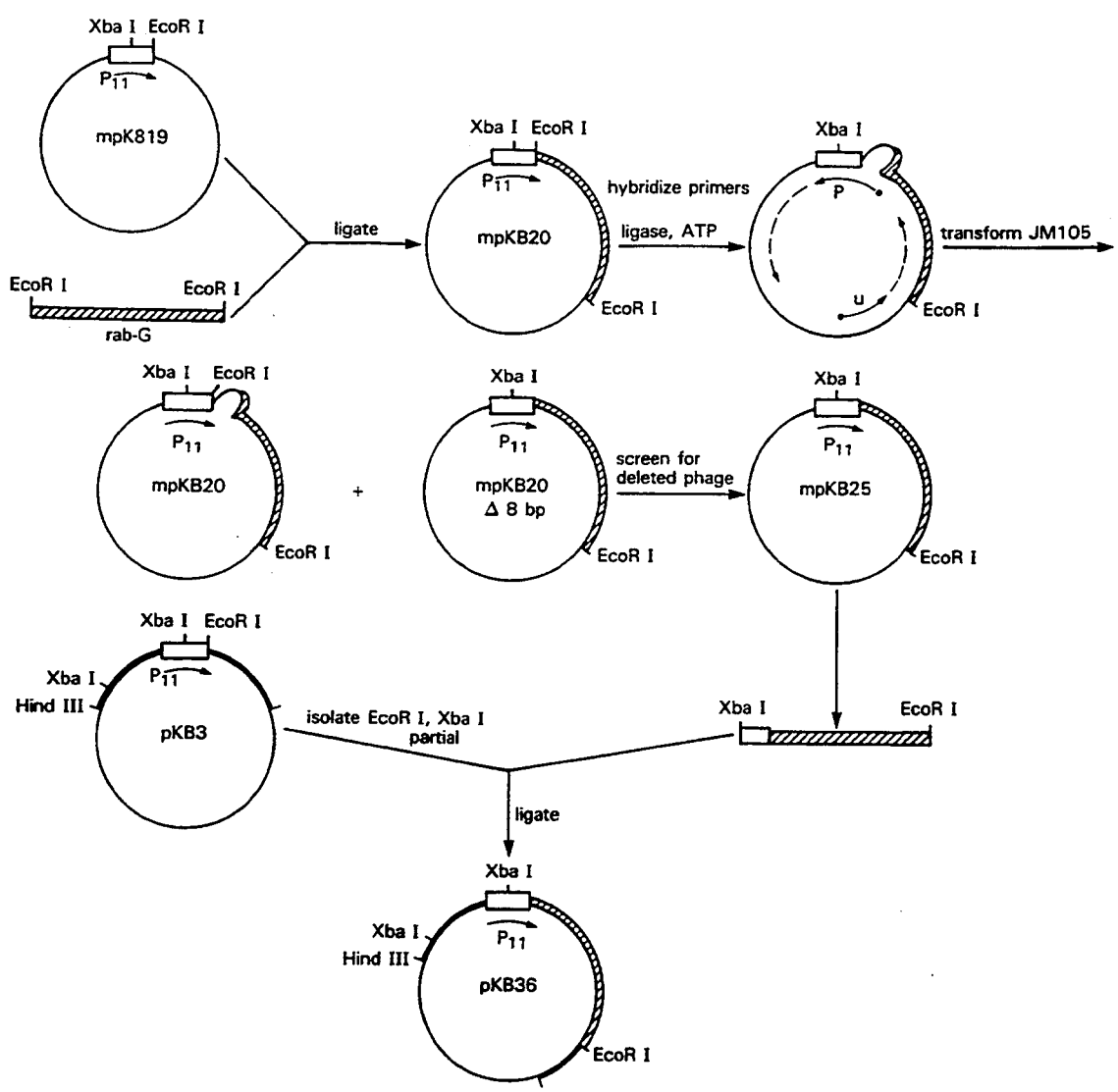

The cloning strategies that were used for constructing pKB3-JE-13 as well as five other vectors containing the 1650 bp G-DNA fragment fused to $P_{7.5}$ or $P_{11}$ promoters derived from the vaccinia virus genes for the 7.5 kD and 11 kD proteins, respectively are depicted in FIG. 1. Routine recombinant DNA manipulations were performed as described by Mackett et al., 1984, J. Virol. 49:857-864; Moss et al., 1983, Eukaryotic Viral Vectors, Elsevier North Holland, N.Y., pp. 201-213. The vector pGS62 (FIG. 1A) is a derivative of pGS20 (Mackett et al. ibid.) with a single EcoRI site downstream of $P_{7.5}$ and the 7.5 kD gene mRNA start site. Although the EcoRI fragment containing the G coding sequence could be inserted directly into the single EcoRI site of pGS62, the nucleotide at the −3 position relative to the ATG adenosine residue is a T (FIG. 2). Since a purine is usually found in this position in eukaryotic (Kozak 1984 Nucl. Acids Res. 12:857-872) and early vaccinia virus genes, the end of the G-DNA was modified by digestion with mung bean nuclease (P-L Laboratories, Inc.; 10 units per 7 pmol DNA ends for 10 min at 35° C. in 50 mM NaCl, 1 mM $ZnCl_2$, 30 mM Na acetate, pH 4.6) and Klenow polymerase 'polishing' the G-DNA blunt ends. A 12 bp EcoRI linker (P-L Laboratories, Inc.) was ligated to the blunt ends and following EcoRI digestion, the released 1650 bp fragment was ligated to EcoRI digested and phosphatase treated pGS62. The sequence of one of the recombinant plasmids pGS62-JE-I (FIG. 2) contained the predicted junction between the vaccinia promoter and G coding segment. The sequence of pGS62-JE-E, however, indicated that some G-DNA had escaped nuclease digestion and linker ligation.

Another set of plasmids were constructed using the vector pKB3 which contains vaccinia TK sequences flanking $P_{11}$. In pKB3 there is a naturally occurring single EcoRI site that is just downstream of $P_{11}$ and the 11 kD gene translation initiation codon and is convenient for foreign gene insertion (FIG. 2). Coding sequences placed here, however, must be in correct reading frame for expression (the ATG adenosine residue is at position +6 relative to the transcript start site). Since direct ligation of G-DNA from pRABpreG into pKB3 would render the G coding sequences out of frame with the vaccinia ATG, mung bean nuclease digestion and addition of 12 bp EcoRI linkers were performed as described above in order to obtain base sequences in correct frame. Two plasmids pKB3-JE-8 and pKB3-JE-13 (FIGS. 1A & 2) were isolated that showed appropriate sequences.

In an alternative strategy (FIG. 1A), the 11 kD protein initiating ATG in vector pKB3 had been changed to AAG by oligonucleotide mutagenesis (Messing 1983 Methods Enzymol 101:20-78), the derived plasmid was designated pKB14 (FIGS. 1A & 2). To insert G coding sequences into pKB14, an EcoRI linker was required only at the carboxyterminal BamHI site of the G-DNA; the resultant vector plasmid was designated pKB26.

Another vector, pKB36, was constructed by oligonucleotide-directed mutagenesis (Adelman et al. 1983 DNA 2:183-193) to fuse $P_{11}$ and the G-DNA (Fig. 1B) in such a way that the G nucleotide sequences replaced the vaccinia 11 kD protein coding sequences (FIG. 2) beginning at the second codon. For this purpose a synthesized 28-mer oligonucleotide (3'-GATAC-GATATTTACCAAGGAGTCCAAGA-5') was used that was complementary to 14 nucleotides on either side of the 8 nucleotides to be deleted.

Using techniques similar to those mentioned herein, plasmids, bacteriophage (Smith et al., 1983, Gene; 25:21–28), yeast (Earl et al., 1986, PNAS, 83:3659–3664), and the like could be used as alternate vectors for recombination of DNA into vaccinia virus.

Formation of recombinant vaccinia viruses

Vaccinia virus infected CV-1 cell monolayers were separately transfected with the six G-DNA vector plasmids described in FIGS. 1 and 2 and analyzed for production of TK-viruses by plaque assay in 143 B cells (Moss et al., 1983, Eukaryotic Viral Vectors. Elsevier North Holland, N.Y.). Lysates of cell monolayers (16 mm² 24-well multidish, Linbro, Inc.) infected with individual plaque isolates were screened for the presence of G-DNA by DNA blot hybridization (Kafatos et al., 1979 Nucleic Acids Res. 7:1541–1552) and for antigen by monoclonal antibody (mAb) assay (Johnson et al. 1984 Gene Anal. Tech. 1:3–8). Prior to production of recombinant virus stocks, immunoblot positive plaque isolates were plaque purified two additional times. Correct insertion of G-DNA into the TK locus was verified by hybridization (Esposito et al. 1985 Virology 143:230–251) of labeled probes to purified viral DNA HindIII digest fragments (Esposito et al. 1981J. Virol. Methods 2:175–179).

Antigen assays

Rabbit serum raised against the supernatant fraction (surface spikes) of NP-40 detergent (Bethesda Research Labs., Inc.) treated purified CVS rabiesvirions or viral monoclonal antibody mouse ascites fluid (both sera capable of neutralizing CVS rabiesvirus) were used to detect G antigen. Western blot assays used for examining G antigen in recombinant infected cells were done as described by Towbin et al., 1984, J. Immunol. Meth. 55:297–307. Radio-iodinated protein A (Amersham, Inc.) was used to detect antibody reactivity in both Western and dot immunoblot assays. Direct immunofluorescence (FA) examination of infected, live, post-fixed cells and acetone fixed cells was performed as described by Wiktor et al. 1978 Proc. Natl. Acad. Sci. 75:3938–3942. Chamber slide (Labtek, Inc.) monolayers of infected CV-1 cells were used for FA microscopic examination of G antigen. HeLa-S3 cells were used for flow cytometer analyses of the surface of recombinant infected cells. For this, infected cells were washed twice (1500 rpm, 10 min) ice-cold phosphate buffered saline (PBS) containing 0.1% bovine serum albumin (BSA) and then resuspended and incubated 45 min at 4° C. in fluorescein-conjugated mAb appropriately diluted in cold PBS containing 0.1% BSA. Cells were then washed twice in cold PBS without BSA. Final cell pellets were vortexed while a cold fixative solution (1% paraformaldehyde in 0.15 M NaCl) was added. Fixed cells ($10^6$ per ml) were then analyzed with a fluorescence activated cell sorter (FACS-IV, Becton Dickenson, Inc.).

Immunization, Antibody Titration, Rabiesvirus Challenge

Four to five-week-old ICR mice (colony bred) and A/J inbred mice (Jackson Laboratories, Inc.) were immunized by footpad inoculation or intradermal scarification with approximately $10^8$ plaque-forming-units (PFU) per 25 ul of sucrose velocity gradient purified NYBH or recombinant virions. Production of CVS virus neutralizing antibody in mice was followed by the rapid fluorescent focus inhibition assay (Reagan et al., 1983, J. Virol. 48:660–666; Smith et al., 1973, Bull. World Health Org. 48:535–541). Mice were challenged with rabiesvirus as detailed in Table 2.

As shown in FIG. 2, two classes of promoter-gene constructs were prepared. In one class, the first potential initiation ATG codon derived from the G-DNA sequences to ensure synthesis of authentic products. Both of the $P_{7.5}$ constructs, pGS62-JE-E and pGS62-JE-I, were designed to make the authentic rabiesvirus G precursor but differed slightly in their mRNA leaders. Of the two, pGS62-JE-I has a sequence that is closer to the consensus found upstream of the eukaryotic translation initiation codon. Similarly, two of the $P_{11}$ constructs, pKB26 and pKB36, have the translation initiation codon of the rabiesvirus gene immediately downstream of the vaccinia virus mRNA start site. They differ in that pKB36 was constructed so that starting at the second codon, the G coding sequence precisely replaces the vaccinia virus 11 kD protein coding sequence. Thus, the short 11 kD vaccinia virus leader mRNA sequence is unaltered yet authentic rabiesvirus G precursor is formed. In pKB26, the T of the 11 kD gene initiation codon was changed to an A thereby causing a slightly longer mRNA leader before the rabiesvirus G initiation codon. In the second class, the initial translation codons were derived from the vaccinia virus 11 kD gene and linker sequences thereby leading to the production of a fusion protein. Despite this, authentic mature G is still made, provided the longer signal peptide is cleaved. Recombinant viruses derived with pKB3-JE-8 and pKB3-JE-13 differ from the others in that they produce fusion proteins that have additional amino acids preceding the signal peptide of the complete precursor G.

Figure 3:
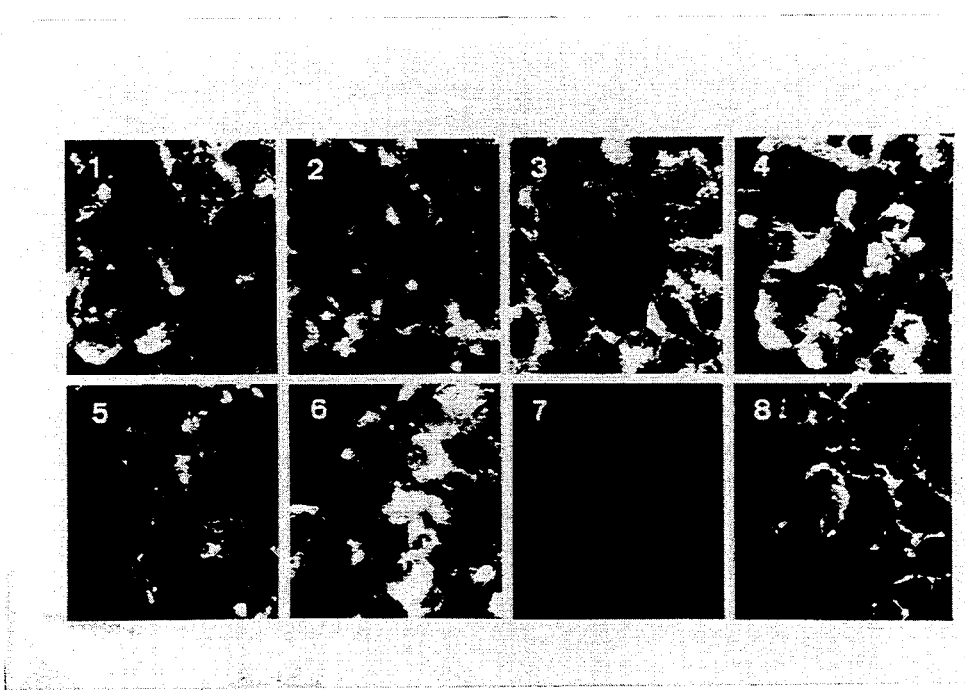

Synthesis of rabiesvirus G was detected by immunofluorescent staining of recombinant virus infected CV-1 cells (FIG. 3). In acetone fixed cells, mAb reacted with G antigen in the cytoplasm (FIG. 3, panels 1–7), whereas surface fluorescence was discerned in unpermeabilized infected cells (panel 8). The latter result indicated that G was transported to the plasma membrane as occurs during rabiesvirus infection. Since surface fluorescence was detected with all recombinant viruses, even the predicted fusion signal peptides appeared to have been correctly processed. The degree of fluorescence was used to semi-quantitate the levels of G expression in cells infected with the various recombinant viruses. Visual inspection of the photographs in FIG. 3 indicated that cells infected with the $P_{7.5}$ recombinants (panels 1 and 2) contained less G antigen than three (panels 3, 4 and 6) of the four $P_{11}$ types. The least amount of G was apparent in cells infected with vKB26 (panel 5).

The relative amounts of plasma membrane G antigen was quantitated by flow cytometry of infected HeLa S-3 cells that had been directly stained with fluorescein conjugated mAb (Table 1). The mean peak fluroescence intensity values (MPI) within cytometer fluorescence intensity channels 71–150 and values of cell counts (% total area) were determined for HeLa cell spinner cultures at 18 h after infection with 25 PFU per cell of each recombinant virus. Background FA values of 4% and 34.8% were obtained with uninfected and parental NYBH strain vaccinia virus infected cells, respectively. The latter may result from alterations in permeability of infected cells. Because the MPI values in Table 1 are linear measures of the log value of fluorescence, a difference of 10 for example, equates to a 10-fold difference in brightness. These values for relative surface expression of G antigen correlated with the amounts of intracellular G estimated by FA staining of acetone fixed cells and by Western blot. Cells infected with recombinants vKB3-JE-8, vKB3-JE-13 and vKB46 showed 6 to 10-fold higher MPI compared to $P_b$ 7.5 recombinants and 100-fold higher MPI than vKB26 infected cells. In separate experiments, infection of cells at a multiplicity of 1 (Table 1, lower section) resulted in MPI values essentially similar to those infected at the higher multiplicity although the percentage of positive cells was less.

TABLE 1

Relative cell surface immunofluorescence of HeLa-S3 cells infected with NYBH vaccinia - rabiesvirus glycoprotein recombinant viruses at 18 h postinfection.

| Virus | Mean peak[a] | % Total area[b] | % Minus background[c] |
|---|---|---|---|
| MOI = 25 | | | |
| vGS62-JE-E | 90.3 | 89.4 | 54.6 |
| vGS62-JE-i | 94.0 | 86.0 | 51.2 |
| vKB3-JE-8 | 99.2 | 67.0 | 32.2 |
| vKB3-JE-13 | 99.0 | 75.5 | 40.7 |
| vKB26 | 88.4 | 78.6 | 43.8 |
| vKB36 | 99.9 | 79.5 | 44.7 |
| NYBH | 87.3 | 34.8 | 0.0 |
| Mock infected | 97.7 | 4.0 | — |
| MOI = 1 | | | |
| vGS62-JE-E | 90.0 | 9.3 | 4.2 |
| vGS62-JE-I | 89.6 | 10.8 | 5.7 |
| vKB3-JE-8 | 97.1 | 8.9 | 3.8 |
| vKB3-JE-13 | 95.9 | 9.9 | 4.8 |
| vKB26 | 89.4 | 14.6 | 9.5 |
| vKB36 | 97.7 | 17.6 | 12.5 |
| NYBH | 90.8 | 5.1 | 0.0 |
| Mock infected | 97.7 | 4.0 | — |

[a]Fluorescent antibody cell sorter (FACS-IV) determined value of immunofluorescence intensity mean peak (linear) within channels 71 to 150 ($10^5$ cells counted). Flow cytometer was calibrated to 10 linear channels (250 total channels) equal 1 decade of log fluorescence. Direct cell surface immunofluorescence reaction was done with a fluorescein conjugated IgG preparation of monoclonal antibody (ascites fluid) against CVS rabiesvirus glycoprotein and cells infected at the indicated multiplicity of infection (MOI).
[b]Percentage immunofluorescent cells determined within channels 71 to 150.
[c]Percentage immunofluorescent cells less background NYBH vaccinia infected cells.

Figure 4:
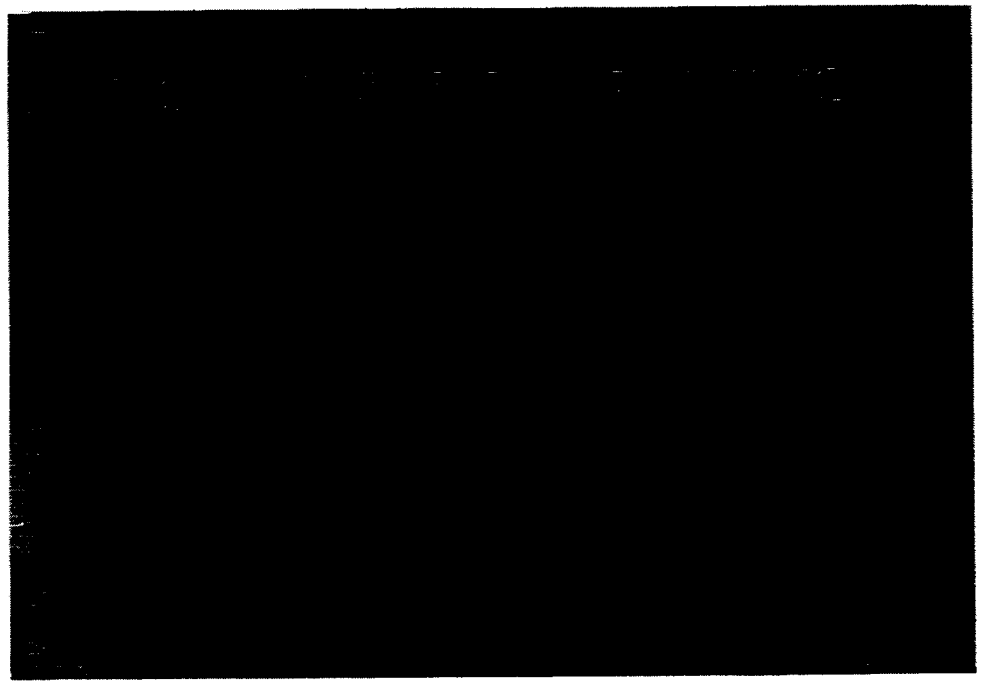

The electrophoretic mobility of G antigen made in cells infected with recombinant viruses was similar to that made in cells infected with rabiesvirus (FIG. 4). With shorter autoradiographic exposure, both completely glycosylated and incompletely glycosylated forms of G (G1 = 64 kD and G2 = 62 kD) (Wunner et al. 1985 Virology 140:1-12) were resolved (results not shown). Monolayers of 143 B cells at 18 h after infection with a multiplicity of 25 PFU of vaccinia virus recombinants vKB3-JE-8, vKB3-JE-13, and vKB36 contained approximately 5-fold more G-antigen than cells infected with equivalent amounts of vGS62-JE-E or vGS62-JE-I,, and at least 25-fold more than cells infected with vKB26. The relative amount of G present in cells infected with the highest expressing recombinant of the present invention were about 250 times higher than in NA cells 44 h after infection with rabiesvirus at a multiplicity of 2. The time course of G antigen synthesis was determined by Sepharose protein-A mAb immunoprecipitation of $^{35}S$-methionine labeled proteins from recombinant virus infected cells. In accordance with the nature of the promoters, G-antigen under control of $P_{7.5}$ was detected about 1 to 2 hr earlier than G-antigen under control of $P_{11}$ (resolved at 4 hr postinfection; not shown).

The potential of recombinant vaccinia viruses to induce neutralizing antibody and protectively immunize mice against lethal rabiesvirus infection is shown in (Table 2). Tests were carried out by vaccinating 5-week-old colony bred ICR mice with a range of concentrations of vKB3-JE-8 and vKB3-JE-13. Inoculations

TABLE 2

Rabiesvirus neutralizing antibody titer (reciprocal) and resistance to challenge of mice immunized by intradermal or footpad inoculation with rabiesvirus glycoprotein vaccinia recombinants.

| | ICR Mice[a] | | | | A/J Mice[b] | | | |
|---|---|---|---|---|---|---|---|---|
| | Log | Titer | | Rabies | Log | Titer | | Rabies |
| Virus | Dose | Median | (Range) | Deaths | Dose | Median | (Range) | Deaths |
| Intradermal | | | | | | | | |
| vKB3-JE-8 | 8.0 | 280 | (250–280) | 0/9 | 8.0 | 5700 | (1400–7000) | 0/11 |
| | 7.0 | 280 | (210–280) | 0/10 | — | | — | — |
| | 6.0 | 165 | (<5–280) | 3/9 | — | | — | — |
| vKB3-JE-13 | 8.4 | 240 | (230–250) | 0/9 | 8.0 | 5700 | (1400–7000) | 0/12 |
| | 7.4 | 145 | (60–230) | 1/9 | — | | — | — |
| | 6.4 | 8 | (<5–10) | 8/10 | — | | — | — |
| vKB26 | — | | — | — | 8.0 | 1600 | (900–7000) | 0/7 |
| vKB36 | — | | — | — | 8.0 | 2400 | (1400–6000) | 0/9 |
| vGS62-JE-E | — | | — | — | 8.0 | 3125 | (1400–7000) | 0/11 |
| vGS62-JE-I | — | | — | — | 8.0 | 6200 | (1400–7000) | 0/9 |
| NYBH | 8.0 | <5 | | 10/10 | 8.0 | <5 | | 11/11 |
| Footpad | | | | | | | | |
| vKB3-JE-8 | 7.7 | 815 | (230–1400) | 0/9 | 8.0 | 1400 | (1100–1400) | 0/12 |
| | 6.9 | 300 | (280–320) | 4/10 | — | | — | — |
| | 6.0 | 100 | (56–145) | 0/9 | — | | — | — |

TABLE 2-continued Rabiesvirus neutralizing antibody titer (reciprocal) and resistance to challenge of mice immunized by intradermal or footpad inoculation with rabiesvirus glycoprotein vaccinia recombinants.

| Virus | ICR Mice[a] | | | | A/J Mice[b] | | | |
|---|---|---|---|---|---|---|---|---|
| | Log Dose | Titer Median | (Range) | Rabies Deaths | Log Dose | Titer Median | (Range) | Rabies Deaths |
| vKB3-JE-13 | 8.2 | 280 | (280–280) | 1/10 | 8.0 | 1400 | (625–1400) | 0/12 |
| | 7.3 | 280 | (280–280) | 0/10 | — | — | — | — |
| | 6.4 | 168 | (56–280) | 3/9 | — | — | — | — |
| vKB26 | — | — | — | — | 8.0 | 280 | (40–1800) | 0/10 |
| vKB36 | — | — | — | — | 8.0 | 1000 | (280–5100) | 0/9 |
| vGS62-JE-E | — | — | — | — | 8.0 | 1200 | (56–6300) | 0/10 |
| vGS62-JE-I | — | — | — | — | 8.0 | 1400 | (625–3125) | 0/11 |
| NYBH | 8.0 | <5 | | 10/10 | 8.0 | <5 | | 10/10 |

[a]Ten colony bred 5-week-old female ICR mice per group were inoculated with log dose PFU indicated of purified virions in PBS. Four weeks later mice were bled (ocular method) for antibody titration. Mice were challenged 5 weeks later by intracerebral inoculation of 30 MLD$_{50}$ CVS rabiesvirus that caused rabies and death in mice not vaccinated. Ratios represent rabies deaths per number of mice challenged.
[b]Twelve inbred 4-week-old female A/J mice per group were inoculated with log dose PFU indicated of purified virions in PBS. Four weeks later mice were bled (ocular mathod) for antibody titration. Mice were challenged 6 weeks later by footpad inoculation of 10 MLD$_{50}$ street rabiesvirus (Mexico dog strain 2699) that caused rabies and death in mice not vaccinated.

were done by intradermal scarification at the base of the tail or by subcutaneous inoculation into the footpad. Four weeks later, neutralizing antibody titers were determined and the mice were challenged with a potentially lethal intracerebral dose of virulent rabiesvirus. Significant antibody levels and protection were obtained following vaccination with $10^6$ PFU and was nearly complete with higher doses.

Further tests (Table 2) were carried out with an inbred strain of mice (A/J) that are reportedly extremely susceptible to rabiesvirus (Lodmell, et al., 1985, J. Virol. 55:788–795). Thus, it was considered that challenge of A/J mice represents a more severe test of the efficacy of vaccination. It was surprising, however, to discover that the neutralization titers obtained by the intradermal route of inoculation were approximately 20 times higher in A/J mice than in ICR mice. Higher titers also were obtained by the subcutaneous route although the differences were not as pronounced. Recombinant vKB26 that expressed G most poorly in tissue culture cells induced the lowest antibody titers by this route; however, the titers obtained with the other recombinants were quite similar to each other. Significantly, all A/J mice including those immunized with vKB3-JE-13 of the invention were protected against lethal rabiesvirus challenge.

It is clear from the above that the G antigen produced in infected tissue culture cells is authentic because of its reactivity with polyclonal and monoclonal antibody, size on polyacrylamide gels, glycosylation, and transport to the plasma membrane. Furthermore, mice immunized with each recombinant virus produced rabiesvirus neutralizing antibody that correlated with protection against lethal rabiesvirus challenge.

It is noted that the construction of recombinant viruses with the present invention (plasmid vector pKB3-JE-13) is unique in several respects such as the strain of vaccinia virus used, the source rabiesvirus of the G gene, the promoters used to regulate expression and the higher level of expression obtained thereby. Mass vaccination experiences during the smallpox eradication era suggested that strains of vaccinia virus differed in the incidence of vaccinal side effects that accompanied their use (Arita and Fenner, 1985. Complications of smallpox vaccination, In "Vaccinia Viruses as Vectors for Vaccine Antigens", G. Quinnan editor, pp. 49–60, Elsevier, North Holland, N.Y.; McIntosh, 1985. A Comparative study of four smallpox vaccines in children, In "Vaccinia Viruses as Vectors for Vaccine Antigens," G. Quinnan, editor, pp. 77–84, Elsevier North Holland, N.Y.; Polak, 1973, Int. Symp. on Smallpox Vaccine, 1972 Bilthaven, 19:235–242, Karger Basil). For example, the Copenhagen strain used for constructing a previous rabiesvirus G recombinant was associated with an increased incidence of encephalitic vaccinal complications and also has been shown to be relatively more pathogenic for animals than certain other commonly used strains. Of the vaccine strains that had been most extensively used during smallpox eradication, the calf adapted NYBH and Lister strains showed the least vaccinal side effects. In the present invention, the United States licensed NYBH strain was selected both for its safety record, potency and extensive experience gained on the use of this strain during smallpox eradication.

The promoter $P_{7.5}$ of vaccinia virus has been widely used in recombinant viruses expressing foreign genes. Because present and future attempts at virus attenuation might be correlated with decreased virus replication, it was conceived to test other vaccinia promoters that might provide higher expression levels and thus avoid possible lessened immune responsiveness especially with relatively innocuous vaccinia strains such as NYBH. The 11 kD virion core protein appears to be one of the major components of vaccinia virus, suggesting that the promoter of this gene might be exceptionally active. Fusion of foreign genes downstream of the mRNA start site and translation initiation codon of the 11 kD gene required appropriate in frame insertion of inserted cDNA coding sequences. Hence, three approaches were taken in constructing $P_{11}$ type vectors. One was to modify the 11 kD protein initiation ATG codon to AAG and thereby construct a longer RNA leader (vKB26). The second was to maintain the ATG of the vaccinia virus gene and use nuclease treatment and linkers to fuse the 11 kD sequences in frame with the coding sequences for G protein; this resulted in formation of a fusion protein containing a signal peptide with three or four extra amino acids (respectively vKB3-JE-8, vKB3-JE-13). The third strategy was to use oligonucleotide-directed mutagenesis to precisely place the G sequences at the 11 kD protein translation start site, thereby retaining the naturally occurring vaccinia leader (vKB36). The G expression levels obtained with $P_{11}$ type recombinants were at least 5-fold higher than with the $P_{7.5}$ type when either the second or third strategies were used. The lowest expression of all, however, was found with vKB26 derived with vector pKB26 constructed with the first approach. Analyses of rabiesvirus glycoprotein expression levels indicated that maintenance of the highly conserved TAAATG sequence around the closely spaced putative transcriptional and translational start sites of the 11 kD late gene was important.

The proper presentation of rabiesvirus G at the plasma membrane appears to be extremely important for vaccinal immunogenicity. Proper processing and plasma membrane insertion of G with recombinants described herein was apparent even with constructs with the signal, peptide containing three or four additional aminoterminal amino acids. Bacterial expressed G never induced production of neutralizing antibodies or protection (Lathe et al., 1985 J. Mol. Appl. Genet. 2:331–342; Malek et al., 1984 Cold Spring Harbor Laboratory, Cold Spring Harbor, N.Y., 1:203–208; Yelverton et al., 1983 Science, 219:614–620).

Of course, a potent and efficacious pharmaceutical composition including a vaccine comprising immunogenic amount of the recombinant vaccinia virus of the present invention in a pharmaceutically acceptable carrier, such as physiological saline or non-toxic buffers and the like is now made possible. An advantage of the antirabies vaccine of the present invention is indeed use of a vaccinia strain of established low vaccinal side effects and the increased level of expression of the G antigen because of regulation by a late promotor, such as $P_{11}$.

Of course, the plasmid vector of the present invention can also be used in poxviruses other than the vaccinia, such as the cowpox, racoonpox and the like following standard techniques well known in the art. Furthermore, diagnostic test kits comprising the rabiesvirus G antigen and/or antibodies (monoclonal or polyclonal) produced against said G antigen by standard procedures well known in the art, can also be prepared to detect or screen for rabiesvirus infection or immunity. Other immuno-reagents, such as specific cytotoxic T cells and the like can also be prepared or made available by employing any of the several embodiments of the present invention as mentioned herein.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A plasmid having recombinant DNA comprising a rabies virus glycoprotein G gene operatively linked to a vaccinia $P_{11}$ late promoter.

2. The plasmid of claim 1 wherein the rabies virus glycoprotein G gene is from Challenge Virus Standard strain.

3. The plasmid of claim 1 having all the identifying characteristics of ATCC 40280.

4. A poxvirus recombinant having incorporated therein a rabies virus glycoprotein G gene operatively linked to a vaccinia $P_{11}$ late promoter.

5. The poxvirus of claim 4 wherein said poxvirus is the New York City Board of health strain of Vaccinia virus.

6. A pharmaceutical composition comprising an immunogenic amount of the recombinant of claims 4 in a pharmaceutically acceptable carrier.

7. A method of inducing protective immunity against rabiesvirus infection in a host comprising administering to a host, susceptible to rabiesvirus infection, an immunogenic amount of recombinant of claim 4 to produce protective immunity against rabiesvirus in said host.

8. The poxvirus of claim 4, wherein said poxvirus is an orthopoxvirus.

9. The poxvirus of claim 8, wherein said orthopoxvirus is cowpox virus.

10. The poxvirus of claim 4, wherein said gene and said promoter are inserted into the TK locus of said poxvirus.

11. The poxvirus recombinant of claim 4, which, when infected into cell culture, expresses both completely glycosylated and incompletely glycosylated forms of said glycoprotein.

12. The poxvirus of claim 4, wherein the DNA sequence coding for glycoprotein G is precisely placed at the 11 kd protein translation start site to thereby retain a naturally occurring vaccinia leader.

13. The poxvirus of claim 4, which is vKB3-JE-8.

14. The poxvirus of claim 4, which is vKB3-JE-13.

15. The poxvirus of claim 4, which is vKB36.

16. An NYBH strain poxvirus recombinant capable of expressing rabies virus glycoprotein G from Challenge Virus Standard Strain under control of promoter $P_{11}$.

17. A method for inducing protective immunity against rabies virus infection in a mammal comprising administering to a mammal, susceptible to rabies an effective amount of the poxvirus recombinant of claim 4, under conditions which allow said poxvirus to infect said mammal and express glycoprotein G under control of said promoter.

18. The method of claim 17, wherein said poxvirus is vKB3-JE-13.

19. The poxvirus of claim 4, comprising a poxvirus $P_{11}$ promoter positioned upstream of a gene for the precursor of the mature glycoprotein G of rabies virus by a short intervening sequence of DNA, wherein said intervening sequence provides an ATG codon sufficient for translational initiation and additional nucleotide residues such that the precursor gene remains in the proper translational reading frame with respect to the translational initiator codon and retains the coding sequences of the precursor protein required for proper intracellular processing, such that the mature glycoprotein G is obtained upon expression of the precursor gene in cells infected with said poxvirus.

20. A composition of matter comprising a recombinant poxvirus of claim 8 in a pharmaceutical carrier.

* * * * *